(12) United States Patent
Zesiewicz et al.

(10) Patent No.: US 12,089,946 B1
(45) Date of Patent: Sep. 17, 2024

(54) SYSTEMS AND METHODS FOR FINGER-TO-THUMB CREASE TESTING

(71) Applicant: UNIVERSITY OF SOUTH FLORIDA, Tampa, FL (US)

(72) Inventors: Theresa Ann Zesiewicz, Oldsmar, FL (US); Kyle Brandon Reed, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 1545 days.

(21) Appl. No.: 16/358,793

(22) Filed: Mar. 20, 2019

(51) Int. Cl.
A61B 5/00 (2006.01)

(52) U.S. Cl.
CPC .......... *A61B 5/4076* (2013.01); *A61B 5/4064* (2013.01); *A61B 5/4824* (2013.01); *A61B 5/6826* (2013.01); *A61B 5/0048* (2013.01)

(58) Field of Classification Search
CPC ... A61B 5/4076; A61B 5/4064; A61B 5/4824; A61B 5/6826; A61B 5/0048
See application file for complete search history.

(56) References Cited

U.S. PATENT DOCUMENTS

| | | | |
|---|---|---|---|
| 9,615,776 B2* | 4/2017 | Smith | G06F 18/2111 |
| 11,064,914 B2* | 7/2021 | Kandori | A61B 5/4088 |
| 2002/0135307 A1* | 9/2002 | Cousy | G05B 19/425 |
| | | | 315/76 |
| 2009/0118648 A1* | 5/2009 | Kandori | A61B 5/1107 |
| | | | 600/595 |
| 2016/0070349 A1* | 3/2016 | Marrs | H01H 13/00 |
| | | | 427/126.3 |

OTHER PUBLICATIONS

Marsden, et al. "Cerebellar ataxia: pathophysiology and rehabilitation" Clin Rehabil 2011 25: 195; Sage Publications.
Giangiardi, et al., "Functional capacity and motor performance of upper limbs in individuals with cerebellar disorders: A pilot study", Hindawi, Behavioural Neurology, vol. 2017, Article ID 8980103.
Gagnon, et al., "Standardized Finger-Nose Test Validity for Coordination Assessment in an Ataxic Disorder", Can J. Neurol. Sci. 20114; 31.
Tilney, et al., "Muscular Coordination Experimentally Studied in its Relation to the Cerebellum", Arch NeurPsych. 1925;13(3):289-334. doi:10.1001/archneurpsyc.1925.02200090003001.
Diener, et al., "Pathophysiology of Cerebellar Ataxia", Movement Disorders, vol. 7, No. 2, 1992.

* cited by examiner

*Primary Examiner* — Charles A Marmor, II
*Assistant Examiner* — Meghan R Kumar
(74) *Attorney, Agent, or Firm* — Quarles & Brady LLP

(57) ABSTRACT

In one embodiment, a system for finger-to-thumb crease testing includes a patient interface configured to attach to a thumb of a patient, the patient interface including a touch sensor configured to sense contact between a finger of the patient and the touch sensor, the touch sensor being positioned on the patient interface in a location at which it overlies a distalmost thumb crease of the thumb when the patient interface is attached, and a control module in electrical communication with the patient interface, the control module being configured to count a number of times the patient successfully taps the touch sensor with the finger.

13 Claims, 3 Drawing Sheets

SYSTEMS AND METHODS FOR FINGER-TO-THUMB CREASE TESTING

BACKGROUND

The finger-to-thumb crease test is a test of upper limb coordination and is often used to evaluate the integrity of the cerebellum. In the test, a patient is requested to repeatedly tap the distalmost crease of the thumb with a finger (e.g., middle finger) of the same hand within a finite period of time, such as 6 seconds. In conducting the test, a medical practitioner (e.g., physician, nurse, or physical therapist) watches the patient perform the taps and manually counts the number of times the patient successfully touches the tip of the finger to the thumb crease. The practitioner then records the total number of successful taps and can use this information, often along with other test data, to assess the health of the patient's cerebellum.

While this form of testing can provide the practitioner with an idea of the functioning of the patient's cerebellum, it is imprecise as it relies on the practitioner's subjective impressions of whether a tap is made in the correct location and therefore counts, or is not made in the correct location and therefore does not count. Because of this imprecision, it can be appreciated that it would be desirable to have systems and methods for finger-to-thumb crease testing that are more precise and yield more accurate results.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have systems and methods for finger-to-thumb crease testing that are precise and yield accurate results. Disclosed herein are examples of such systems and methods. In one embodiment, a system for finger-to-thumb crease testing comprises a patient interface that can be applied to a patient's thumb. The patient interface includes a touch sensor that is positioned over the distalmost thumb crease. The patient interface and, more particularly, its touch sensor, is in electrical communication with a control module. The control module can be used to start and stop an evaluation session in which the patient taps the touch sensor, and therefore the distalmost thumb crease, as many times as he or she can in a predetermined time period. The control module automatically counts each successful tap that is registered by the touch sensor. Once the predetermined time period has passed, the control module can display, store, and/or transmit the total number of successful taps, which can be considered in assessing the integrity of the patient's cerebellum. As the system automatically detects successful thumb taps, and does not detect unsuccessful taps, the subjectivity of the prior art test is removed and more accurate results are obtained.

In the following disclosure, various specific embodiments are described. It is to be understood that those embodiments are example implementations of the disclosed inventions and that alternative embodiments are possible. Such alternative embodiments include hybrid embodiments that include features from different disclosed embodiments. All such embodiments are intended to fall within the scope of this disclosure.

The disclosed systems and methods enable more precise finger-to-thumb crease testing by electronically sensing finger taps with precision. Such sensing removes the opportunity for judgement errors that would otherwise be made by the individual (e.g., medical practitioner) administering the test. Accordingly, more accurate results can be obtained and, therefore, more accurate assessments can be made about the functioning of the patient's cerebellum.

Figure 1:
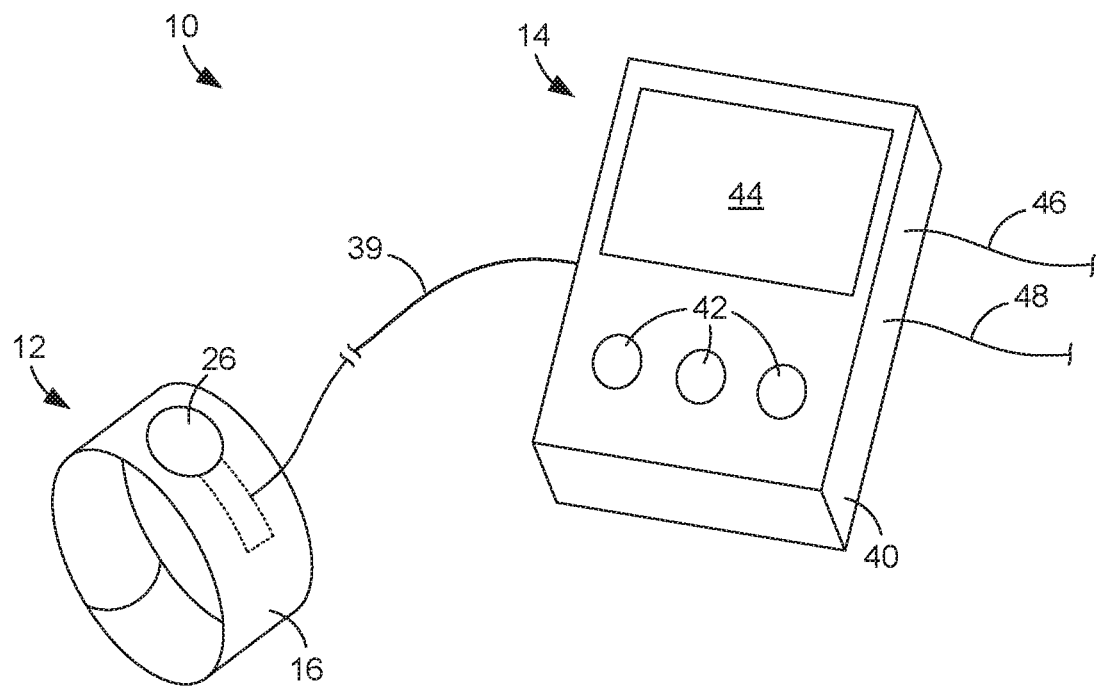
FIG. 1 is a schematic view of an embodiment of a system for finger-to-thumb crease testing.
Figure 2:
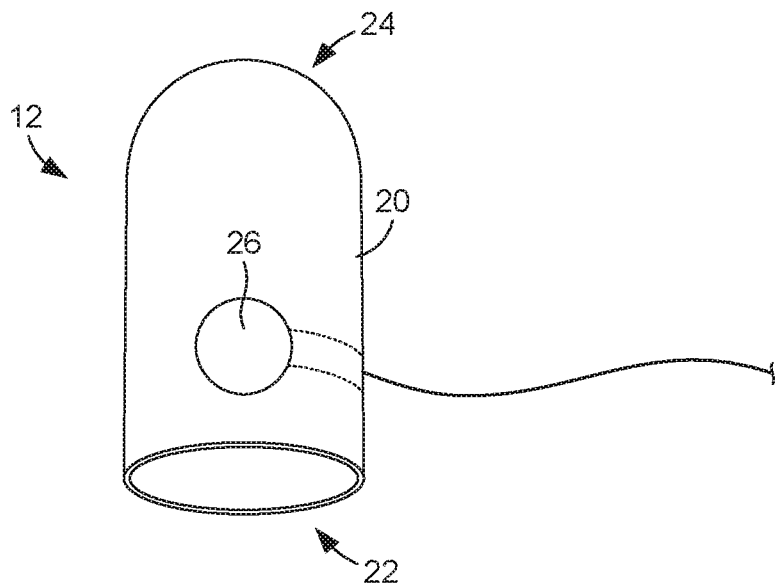
FIG. 2 is a side view of an alternative patient interface that can be used in the system of FIG. 1.

FIG. 1 illustrates an example embodiment of a system 10 for finger-to-thumb crease testing. As shown in this figure, the system 10 generally comprises a patient interface 12 and a control module 14. The patient interface 12 is configured to attach to a patient's thumb at its distalmost crease, which is located at the interphalangeal joint. In the example of FIG. 1, the patient interface 12 comprises a band 16 that can be wrapped around the thumb. The band 16 can be made of a flexible material, such as a fabric or polymeric material, and, in some embodiments, can be elastic. The band 18 can comprise a continuous (endless) band that can be slid over the patient's thumb, or can be a non-continuous band, in which case the band has opposed free ends that can be connected together with suitable fastening elements, such as hook and loop fasteners, snaps, a buckle, or the like. In an alternative embodiment illustrated in FIG. 2, the patient interface 12 can comprise a small sleeve 20 that is configured to be slipped onto the end of the thumb. As shown in FIG. 2, the sleeve 20 can be configured as a finger cot having a generally cylindrical shape with one open end 22 into which the thumb can be inserted, and an opposed closed end 24. Like the band 16, the sleeve 20 can be made of a flexible material, such as a fabric or polymeric material, and, in some embodiments, can be elastic.

Figure 3:
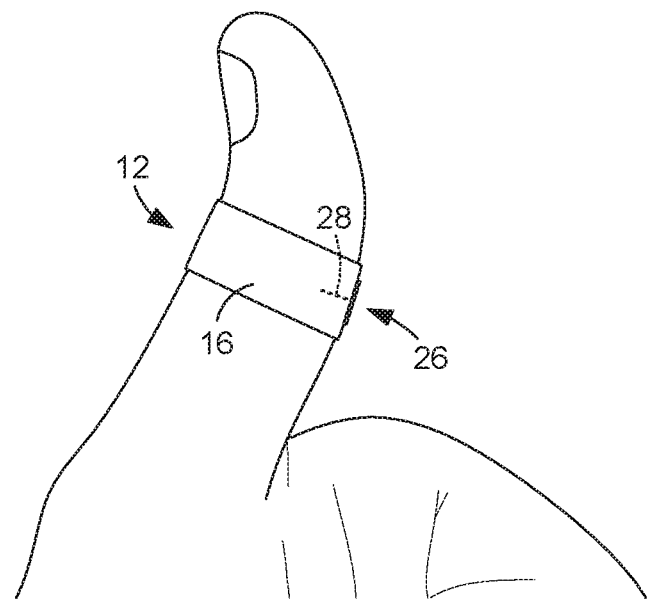
FIG. 3 is a side view illustrating a patient interface shown in FIG. 1 attached to patient's thumb.

Irrespective of the nature of the patient interface 12, the interface includes a touch sensor 26 that is configured to detect contact, and more particularly finger taps, from the patient's finger (e.g., middle finger). The touch sensor 26 is positioned on the outer surface of the patient interface 12 in a location that overlies the patient's distalmost thumb crease when the interface is applied to the thumb. FIG. 3 illustrates an example of this in the case in which the patient interface is the band 16 shown in FIG. 1. As is apparent in FIG. 3, the band 16 is wrapped about the thumb so that the touch sensor 26 overlies the distalmost thumb crease, which is identified by dashed line 28.

Figure 4:
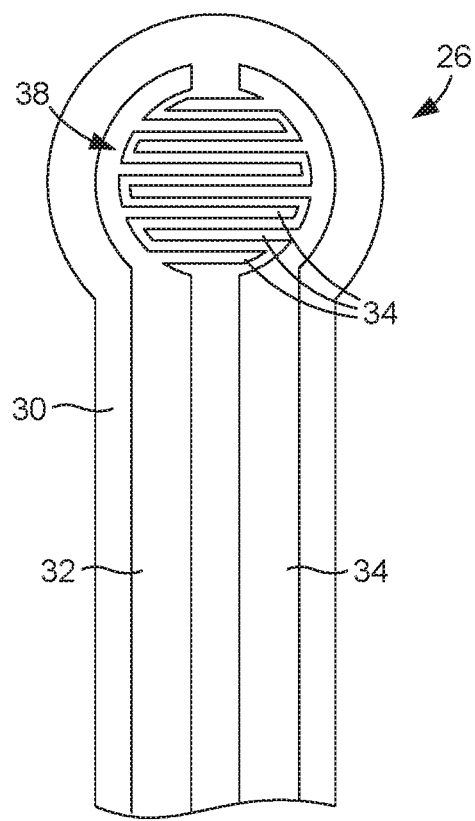
FIG. 4 is a top view of an embodiment of a touch sensor that can be used in a patient interface used in the system of FIG. 1.

The touch sensor 26 can take a variety of forms. In some embodiments, the touch sensor 26 comprises unconnected contacts of a circuit that is normally in an "open" condition, but that becomes a "closed" circuit when the pad of the fingertip touches both contacts simultaneously. FIG. 4 shows an example of such a touch sensor 26. In this figure, the touch sensor 26 comprises a thin, flexible substrate 30 on which two unconnected contacts 32 and 34 are provided.

Each contact 32, 34 comprises a plurality of elements or "fingers" 36 that are located within a sensing zone 38 of the sensor 26, which is placed directly over the thumb crease. In some embodiments, this sensing zone 38 can be approximately 10 to 100 mm$^2$ in area. The fingers 36 of the two contacts 32, 34 are interleaved with each other in an alternating fashion with each finger of one contact being adjacent to one or two fingers of the other contact. When a fingertip contacts these interleaved fingers 36, the conductivity of the fingertip closes the circuit between the two contacts 32, 34 and a successful tap is registered.

In other embodiments, the touch sensor 26 can comprise a force sensor, such as a force transducer that, for example, comprises one or more strain gauges, a piezoelectric element, a resistive element, or a capacitive element. In such a case, the touch sensor 26 can register a successful tap when the fingertip is applied to the sensor with a force that meets or exceeds a predetermined threshold.

With reference back to FIG. 1, the patient interface 12 and, more particularly, the touch sensor 26 it supports, is placed in electrical communication with the control module 14 with a cable 39. The control module 14 is used to control operation of the system 10 and to collect data, in the form of successful taps, sensed by the touch sensor 26. As shown in FIG. 1, the control module 14 can comprise an outer housing 40 that supports a user interface that includes user input devices, such as one or more buttons 42, and a display 44, which can, for example, comprise a liquid crystal display (LCD). The buttons 42 can be used to control operation of the system 10 as a whole and the display 30 can be used to convey information collected by the system to the user (e.g., medical practitioner), as described below. An example configuration for the control module 14 is described below with reference to FIG. 5.

Also shown in FIG. 1 are two further cables 46 and 48 that extend from the control module 14. One of these cables 38 can be used to deliver power (e.g., voltage from a wall outlet) to the control module 14 and the other cable 40 can be used to transmit data to a separate computing device (not shown), such as a desktop computer, notebook computer, tablet computer, smart phone, or other device with computing capability.

Figure 5:
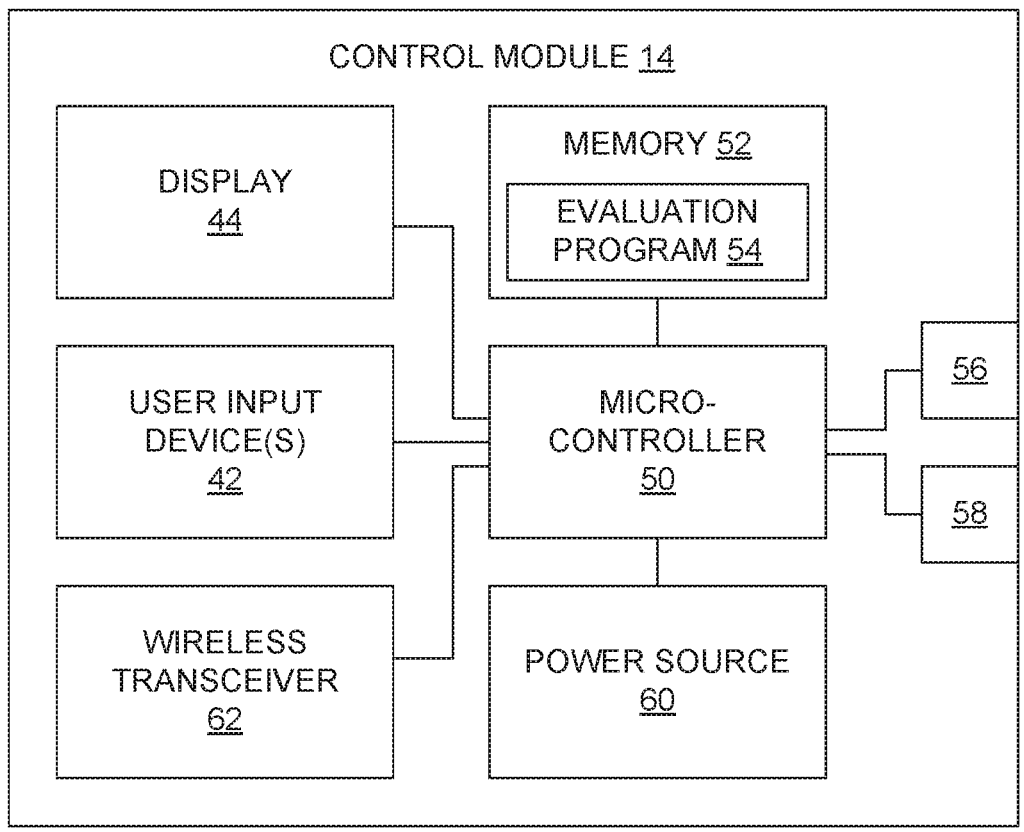
FIG. 5 is a block diagram of an embodiment of the architecture of a control module shown in FIG. 1.

FIG. 5 shows an example architecture for the control module 14. As shown in this figure, in addition to the user input devices (e.g., buttons) 42 and the display 44, the control module 14 can include a microcontroller 50 that controls the operation of the system 10 and memory 52 that stores an evaluation program 54 configured to initiate an evaluation session in which a finger is to be tapped against the thumb crease and to keep a running count of the number of taps that are detected by the touch sensor 26. While the memory 52 is shown as a separate component from the microcontroller 50, it will be appreciated that the memory can, in some embodiments, be integrated with the microcontroller. In addition, the memory 52 can comprise a removable computer-readable medium, such as a memory card.

Also shown in FIG. 5 are electrical ports 56 and 58 that can be used for connection with the cables 46 and 48 shown in FIG. 1. In addition, shown are an optional power source 60, such as a battery, which can be used to power the control module 14, and an optional wireless transceiver 62, which can be used to wirelessly transmit data to the separate computing device.

The system 10 can be used to conduct finger-to-thumb crease tests similar to those performed in the prior art, but with much greater precision and accuracy. To conduct such a test, the control module 14 is powered on, for example, by pressing one of the buttons 42 (e.g., a "power" button). The patient interface 12 is then (or previously) applied to a thumb of the patient in a manner in which the touch sensor 26 is positioned directly over the distalmost thumb crease. For example, the band 18 can be wrapped around the thumb (as in FIG. 3) or the sleeve 24 can be slipped onto the thumb.

Figure 6:
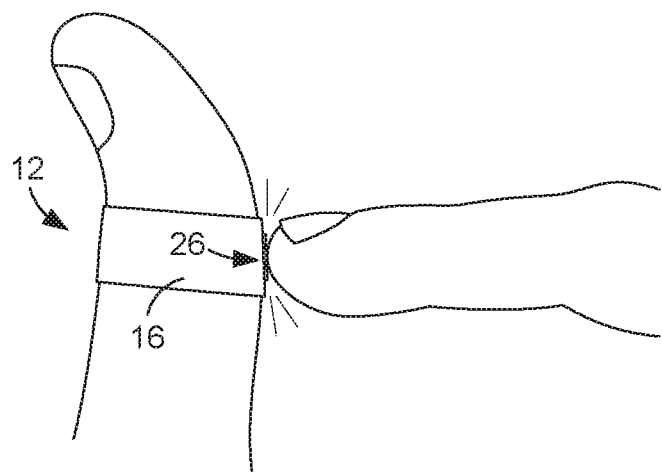
FIG. 6 is a side view illustrating a patient tapping a distalmost thumb crease with a finger with the patient interface in position over the crease.

Once the patient interface 12 has been applied to the patient's thumb, an evaluation session can be conducted. In some embodiments, the session is started by the medical practitioner. For example, the practitioner can request that the patient prepare to perform finger taps on the thumb, for example, using the middle finger, and then can initiate the session using one of the buttons 42 provided on the control module (e.g., using a "start" button). This action will start a timer that will count down a predetermined period of time (e.g., 4-10 seconds, such as 6 seconds) during which the patient will tap the touch sensor 26 as many time as he or she can. Once the session is started, the patient begins tapping the touch sensor 26/thumb crease with the fingertip, as illustrated in FIG. 6.

The touch sensor 26 will register each successful tap as it occurs and transmits a signal to the control module 14 at each such instance. The control module 14, in turn, maintains a count of the number of successful finger taps until the predetermined time period has expired. After that point, no further finger taps will be counted. Once the session has ended, the number of successful finger taps can be displayed in the display 44, stored within memory 52, and/or transmitted to the separate computing device.

While the patient interface 12 has been illustrated and described as comprising a band 18 or a sleeve 24, it is noted that the patient interface can have other configurations. For example, the patient interface 12 could be configured as a glove that comprises a touch sensor 26 that is positioned in the thumb of the glove at a location in which it would overlap the distalmost thumb crease. In such a case, the fingers of the glove can have open tips such that the fingertips are exposed. It is also noted that the disclosed system can further include components that are used to conduct other evaluations relevant to a patient's brain or neurological system health. For example, appropriate vibration elements can be integrated into the glove to evaluate the patient's ability to sense vibrations in the fingers and/or hand for the purpose of performing a neurologic vibratory sense evaluation.

The invention claimed is:

1. A system for finger-to-thumb crease testing, the system comprising:
a patient interface configured to be worn on a thumb of a hand of a patient, the patient interface being configured as a band, sleeve, or glove and including a touch sensor configured to sense contact between a finger of the hand and the touch sensor, the touch sensor being positioned on the patient interface in a location at which it overlies a distalmost thumb crease of the thumb when the patient interface is worn, wherein the touch sensor comprises unconnected electrical contacts of a circuit and wherein the circuit becomes a closed circuit via conductivity of the finger when the finger simultaneously touches the electrical contacts, wherein the unconnected electrical contacts comprise first contacts and second contacts, wherein the first contacts and the second contacts are positioned to be interleaved with one another, and wherein the first contacts and the second contacts are configured to be electrically connected via the conductivity of the finger when the finger simultaneously touches the first contacts and second contacts; and a control module in electrical communication with the patient interface, the control module including a microcontroller, memory that stores an evaluation program configured for execution by the microcontroller, a user interface configured to receive user commands, and a display configured to communicate information about the testing to the user, wherein the control module is configured to count a number of times the patient successfully taps the touch sensor with the finger within a 6-second time period, display the number to the user on the display, and store the number in memory.

2. A system for finger-to-thumb crease testing, the system comprising:

a patient interface configured to attach to a thumb of a patient, the patient interface including a touch sensor configured to sense contact between a finger of the patient and the touch sensor, the touch sensor being positioned on the patient interface in a location at which it overlies a distalmost thumb crease of the thumb when the patient interface is attached, wherein the touch sensor comprises unconnected electrical contacts of a circuit and wherein the circuit becomes a closed circuit via conductivity of the finger when the finger simultaneously touches the electrical contacts, wherein the unconnected electrical contacts comprise first contacts and second contacts, wherein the first contacts and the second contacts are positioned to be interleaved with one another, and wherein the first contacts and the second contacts are configured to be electrically connected via the conductivity of the finger when the finger simultaneously touches the first contacts and second contacts; and a control module in electrical communication with the patient interface, the control module being configured to count a number of times the patient successfully taps the touch sensor with the finger.

3. The system of claim 2, wherein the patient interface comprises a flexible band configured to wrap around the patient's thumb.

4. The system of claim 2, wherein the patient interface comprises a sleeve configured to surround the patient's thumb.

5. The system of claim 2, wherein the patient interface comprises a glove configured to be worn on the patient's hand.

6. The system of claim 2, wherein the control module comprises a microcontroller and memory that stores an evaluation program configured to count the number of times the patient successfully taps the touch sensor with the finger within a predetermined time period.

7. The system of claim 6, wherein the predetermined time period is 4 to 10 seconds.

8. The system of claim 6, wherein the control module further comprises a user interface configured to receive user commands and a display configured to communicate information about the testing to the user.

9. A method for finger-to-thumb crease testing, the method comprising:

applying a touch sensor to a thumb of a patient with the touch sensor overlying a distalmost thumb crease of the thumb, the touch sensor being configured to sense contact between a finger of the patient and the touch sensor, wherein the touch sensor comprises unconnected electrical contacts of a circuit and wherein the circuit becomes a closed circuit via conductivity of the finger when the finger simultaneously touches the electrical contacts, wherein the unconnected electrical contacts comprise first contacts and second contacts, wherein the first contacts and the second contacts are positioned to be interleaved with one another, and wherein the first contacts and the second contacts are configured to be electrically connected via the conductivity of the finger when the finger simultaneously touches the first contacts and second contacts;

electronically sensing each time the patient touches the finger to the touch sensor during a predetermined time period; and determining a total number of times the patient touched the finger to the touch sensor during the predetermined time period.

10. The method of claim 9, wherein applying a touch sensor comprises attaching a patient interface that supports the touch sensor to a body part.

11. The method of claim 10, wherein attaching a patient interface comprises attaching a flexible band to the thumb.

12. The method of claim 10, wherein attaching a patient interface comprises passing a sleeve over the thumb.

13. The method of claim 10, wherein attaching a patient interface comprises placing a glove over the patient's hand.

* * * * *